United States Patent
Gupta

(10) Patent No.: US 6,537,976 B1
(45) Date of Patent: Mar. 25, 2003

(54) DIALYSIS SOLUTIONS CONTAINING WATER SOLUBLE VITAMINS AND NUTRIENTS

(76) Inventor: Ajay Gupta, 39151 Horton, Farmington Hills, MI (US) 48331

(*) Notice: Subject to any disclaimer, the term of this patent is extended or adjusted under 35 U.S.C. 154(b) by 0 days.

(21) Appl. No.: 09/367,629

(22) PCT Filed: Aug. 6, 1998

(86) PCT No.: PCT/US98/16383

§ 371 (c)(1),
(2), (4) Date: Oct. 18, 1999

(87) PCT Pub. No.: WO99/07419

PCT Pub. Date: Feb. 18, 1999

Related U.S. Application Data

(60) Provisional application No. 60/055,015, filed on Aug. 7, 1997.

(51) Int. Cl.[7] ............................................... A61K 31/70
(52) U.S. Cl. ......................................... 514/52; 604/29
(58) Field of Search ........................... 514/52; 604/29; 210/646

(56) References Cited

U.S. PATENT DOCUMENTS

| | | | |
|---|---|---|---|
| 4,237,167 A | 12/1980 | Cavazza | 424/311 |
| 4,272,549 A | 6/1981 | Cavazza | 424/316 |
| 5,108,767 A | 4/1992 | Mulchandani et al. | 426/72 |
| 5,230,996 A | 7/1993 | Rath et al. | 435/1 |
| 5,563,126 A * | 10/1996 | Allen et al. | |
| 5,597,805 A | 1/1997 | Breborowicz et al. | 514/19 |
| 5,635,199 A * | 6/1997 | Trimbo et al. | |
| 5,851,985 A * | 12/1998 | Tepic et al. | |
| 5,985,857 A * | 11/1999 | Hudson et al. | |

OTHER PUBLICATIONS

Caplus abstract (2000:725454) of WO 2000059493. Khalifah et al. (2000), Improved dialysis solutions and methods.*
Ahmad et al. (1990), *Kidney International* 38:912–18.
Allman et al. (1989), *Medical Journal of Australia* 150:130–33.
Bostom et al. (1996), *Kidney International* 49:147–52.
Consensus Group (1994), *Dialysis and Transplantation* 23177–81.
Descombes et al. (1993), *Kidney International* 43:1319–28.
Golper et al. (1990), *Kidney International* 38:904–11.
Kasma et al. (1996), *Am. J. Kidney Dis.* 27:680–686.
*Physician's Desk Reference* (1996), p. 13119 (entry for CARNITOR®.
Ponka et al. (1983), *Acta Medica Scandinavica* 213:305–7.
Pru et al. (1985) *Nephron* 39:112–116.
*Physician's Desk Reference* (1998), p. 2781–83 (entries for CARNITOR®.

* cited by examiner

*Primary Examiner*—Ralph Gitomer
(74) *Attorney, Agent, or Firm*—Drinker Biddle & Reath LLP

(57) ABSTRACT

The invention relates to methods and compositions for the prevention and treatment of vitamin and other nutrient deficiencies in hemodialysis and peritoneal dialysis patients. Patients are dialyzed with a dialysate solution comprising at least one vitamin.

40 Claims, No Drawings

DIALYSIS SOLUTIONS CONTAINING WATER SOLUBLE VITAMINS AND NUTRIENTS

CROSS-REFERENCE TO RELATED APPLICATIONS

This application claims the benefit of U.S. Provisional Application Serial No. 60/055,015, filed Aug. 7, 1997.

FIELD OF THE INVENTION

This invention generally relates to methods and compositions for hemodialysis and peritoneal dialysis. In particular, the invention relates to the use of a dialysate solution comprising at least one vitamin to improve the nutritional status of a dialysis patient.

BACKGROUND OF THE INVENTION

A. Dialysis

Dialysis provides a method for supplementing or replacing renal function in patients with renal failure. Therefore, dialysis helps maintain homeostasis in patients with end stage kidney failure. Dialysis is defined as the movement of solute and water through a semipermeable membrane which separates the patient's blood from the dialysate solution. The semipermeable membrane can either be the peritoneal membrane in peritoneal dialysis patients or an artificial dialyzer membrane in hemodialysis patients. Molecules transfer across this semipermeable membrane by the processes of diffusion and convection. In hemodialysis, the patient's blood is passed through an artificial kidney dialysis machine. A membrane in the machine acts as an artificial kidney for cleansing the blood. Because it is an extracorporeal system that requires special machinery, there are certain inherent disadvantages with hemodialysis.

To overcome the disadvantages associated with hemodialysis, peritoneal dialysis was developed. Peritoneal dialysis utilizes the patient's own peritoneum as a semipermeable membrane. The peritoneum is the membranous lining of the body cavity that due to the large number of blood vessels and capillaries, is capable of acting as a natural semi-permeable membrane. In peritoneal dialysis, a dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. The dialysis solution is then simply drained from the body cavity through the catheter.

Modern hemodialysis machines utilize a sophisticated proportioning system to mix concentrated sodium bicarbonate solution with an acid concentrate solution (containing NaCl, KCl, $CaCl_2$, Na-Acetate, and glucose) and purified water. For example in the widely used Fresenius system, the ratio of acid:bicarbonate:water:total is 1:1.23:32.77:35. Therefore, 1 part of the concentrated bicarbonate solution is mixed with 27.5 parts of the other (acid+water), to make the final dialysate. Concentrated bicarbonate solution is either prepared from powder in the dialysis facility or is supplied by the manufacturer as a ready-made sterile solution. In making the bicarbonate concentrate, purified water is pumped from the water source by a pipe into a large tank. Sodium bicarbonate is supplied as a powder packaged in plastic bags and the contents of each bag are mixed with purified water in the tank, to make 25 gallons (94.6 liters) of bicarbonate solution. After thorough mixing with a stirrer the concentrated solution is dispensed into 20 liter plastic receptacles, that are capped. The non-sterile concentrate is used within 24 hr of its preparation. In dialysis practice bicarbonate concentrate is usually prepared in 25–50 gallon quantities.

Various other compounds, in addition to salts, buffers, and carbohydrates, may be added to dialysate solutions. U.S. Pat. No. 5,230,996 discloses methods and compositions for the treatment and prevention of cardiovascular disease in which ascorbate, binding inhibitors, and antioxidants are added to a hemodialysis solution. U.S. Pat. No. 5,597,805 discloses the addition of dipeptides and free radical scavengers such as vitamin E, procysteine, superoxide dismutase, and chondroitan sulfate to peritoneal dialysis solutions for use during and immediately after an episode of peritonitis. Vitamin C is added to the dialysate solution in some centers in order to neutralize chloramine and prevent hemolytic anemia (Kjellstrand et al. (1974), *Nephron* 13:427–433), but high levels of ascorbic acid in the dialysate may predispose to oxalemia and vascular disease.

B. Vitamin Deficiencies in Dialysis Patients

Patients with chronic renal failure are at an increased risk for multiple vitamin deficiencies. Vitamin intake is often decreased in uremic patients because of anorexia and reduced food intake. Also, the diets prescribed for these patients frequently contain less than the recommended daily allowances for certain water soluble vitamins. The metabolism of folate and pyridoxine is abnormal in renal failure and many drugs have been reported to impair the metabolism and pharmacology of vitamins.

Furthermore, water soluble vitamins are removed by dialysis. In hemodialysis, some of the factors that may influence the degree of loss of a specific vitamin are the size of the vitamin molecule in relation to the pore size of the dialysis membrane, the number of pores, the blood and dialysate flow rate, the duration of dialysis, the aging of the reused membrane, and the specific dialysis fluid composition. In addition, vitamins that are bound to large protein molecules are less likely to pass across the dialysis membrane. In peritoneal dialysis the peritoneum of the patient serves as the dialysis membrane and absorption plays a role in nutrient exchange. Factors influencing the flux of vitamins in peritoneal dialysis include the molalities of the different dialysates, which can affect the activity of specific exchange processes in the peritoneum, and peritonitis or sclerosis of the membrane.

C. Vitamin Supplementation in Dialysis Patients

While fat soluble vitamins are known to accumulate in uremia, deficiencies of water soluble vitamins have been reported in dialysis patients. The prescription of oral water-soluble vitamins is, therefore, a routine practice in many dialysis units.

Among the ten major dialysis centers in Australia for example, Allman reported that an oral supplement of thiamin, riboflavin, pyridoxine, ascorbic acid and nicotinamide was given in all, and folic acid was given in eight of the ten centers (Allman et al. (1989), *Medical Journal of Australia* 150:130–33).

On the other hand, the need for routine vitamin supplementation in dialysis patients has been questioned by some practitioners, based on the facts that hemodialysis patients are no longer on severely restricted diets, that dialysate losses may be lower than previously believed, and that recent studies in patients receiving systematic supplementation showed excessively high vitamin levels. In one study, forty-three chronic hemodialysis patients not prescribed biotin, riboflavin, or vitamin $B_{12}$ supplements were found to maintain normal serum levels of these vitamins for period of one year (Descombes et al. (1993), *Kidney International* 43:1319–28). Furthermore, despite the water solubility of thiamine, riboflavin, pantothenic acid and biotin, these compounds are frequently maintained in the normal range in chronic dialysis patients. It has been postulated that the losses of these vitamins into the dialysate might be offset by the reduction in renal catabolism or urine loss in these patients. Some clinicians therefore believe that no systematic supplement is indicated for biotin, riboflavin, or vitamin $B_{12}$ in maintenance hemodialysis patents. However, vitamin supplementation with ascorbic acid, pyridoxine, and folic acid is needed to correct vitamin deficiencies; and despite an absence of true thiamine deficiency, thiamine supplementation is needed to restore erythrocyte transketolase activity in chronic dialysis patients.

D. Carnitine Deficiencies in Dialysis Patients

Carnitine is an amino acid derivative which is essential for the transport of long-chain fatty acids across the mitochondria, where fatty acids are oxidized to provide energy for muscle and other cells. Signs of carnitine deficiency include muscle weakness, cardiac dysfunction, hypoglycemia, and changes in lipid profile such as elevated triglycerides. Carnitine is water soluble and not highly bound to any large molecule. Carnitine is, therefore, cleared by hemodialysis and peritoneal dialysis.

In a multicenter, double blind, placebo-controlled randomized clinical trial in 82 chronic hemodialysis patients it was reported that 50% of the patients randomized to receive 20 mg/kg intravenous carnitine after each hemodialysis session for a period of 6 months showed global improvement in clinical status, compared with 18% in the control group (Ahmad et al. (1990), *Kidney, International* 38:912–18). Carnitine administration resulted in improvement in intradialytic hypotension, muscle cramps, exercise capacity, a sense of well being, and possibly an increase in muscle mass. Furthermore, L-carnitine deficiency in dialysis patients may promote resistance to erythropoietin action, which is corrected by L-carnitine supplementation.

A consensus group was convened in 1993 at Georgetown University (Washington D.C.) to address use of carnitine in dialysis patients. The group found that carnitine may play an important role in treating certain dialysis patients who fail to respond to standard therapy, and recommended a route and dose of administration of 20 mg/kg body weight intravenously at the end of each dialysis treatment (Consensus Group (1994), *Dialysis and Transplantation* 23:177–81).

Benefits to dialysis patients have been reported after the administration of both oral and intravenous carnitine. In addition, U.S. Pat. Nos. 4,237.167 and 4,272,549 disclose that acyl carnitines and carnitine may be added to dialysis solutions (at levels above the concentration of free carnitine in normal serum) to alleviate asthenia and muscle weakness in chronic uremic patients.

Oral and intravenous supplementation of nutrients in dialysis patients present problems in terms of expense, compliance, and bioavailability. There is a need, therefore, for improved methods and compositions for the prevention and treatment of vitamin and other nutrient deficiencies in dialysis patients.

SUMMARY OF THE INVENTION

The present invention relates to the discovery that vitamins, carnitine, and other nutrients may be advantageously added to dialysate solutions in order to: (1) prevent the loss of vitamins, carnitine, and other nutrients during dialysis, and (2) correct vitamin, carnitine, and other nutrient deficiencies in dialysis patients.

The invention provides a method for preventing or correcting a nutrient deficiency in a dialysis patient comprising dialysis of the patient with a dialysate solution which comprises an effective amount of at least one vitamin selected from the group consisting of folic acid, vitamin $B_6$, thiamine, vitamin $B_{12}$, and pharmaceutically acceptable salts thereof.

In some embodiments the dialysis is hemodialysis, and vitamin deficiencies may be prevented by adding at least a physiological amount of the vitamin to the dialysate solution or corrected by adding a supraphysiologic amount of the vitamin to the dialysate solution.

In some preferred hemodialysis embodiments the dialysate solution comprises: (a) up to 1500 μg/L or up to 15 μg/L folic acid or the equivalent molar amount of a pharmaceutically acceptable salt thereof, (b) up to 100 μg/L or up to 10 μg/L vitamin $B_6$ or the equivalent molar amount of a pharmaceutically acceptable salt thereof, (c) up to 75 μg/L or up to 20 μg/L thiamine or the equivalent molar amount of a pharmaceutically acceptable salt thereof, or (d) up to up to 60 /μg/L or up to 0.6 μg/L vitamin $B_{12}$ or the equivalent molar amount of a pharmaceutically acceptable salt thereof.

In some preferred hemodialysis embodiments the dialysate solution further comprises an effective amount, preferably up to 40 mg/L or up to 15 mg/L, of vitamin C or a pharmaceutically acceptable salt thereof.

In some preferred hemodialysis embodiments the dialysate solution further comprises an effective amount, preferably up to 300 μmol/L or up to 50 μmol/L, of carnitine or a pharmaceutically acceptable salt thereof.

In more preferred hemodialysis embodiments the dialysate solution comprises at least two nutrients or at least three nutrients selected from the group consisting of folic acid, vitamin $B_6$, thiamine, vitamin $B_{12}$, vitamin C, carnitine, and pharmaceutically acceptable salts thereof. In a most preferred embodiment the dialysate solution comprises folic acid, vitamin $B_6$, thiamine, vitamin $B_{12}$, vitamin C, and carnitine, or pharmaceutically acceptable salts thereof.

In other embodiments the dialysis is peritoneal dialysis, and vitamin deficiencies may be prevented by adding at least a physiological amount of the vitamin to the dialysate solution or corrected by adding a supraphysiologic amount of the vitamin to the dialysate solution.

In some preferred peritoneal dialysis embodiments the dialysate solution comprises: (a) up to 15 mg/L folic acid or the equivalent molar amount of a pharmaceutically acceptable salt thereof, (b) up to 10 mg/L vitamin $B_6$ or the equivalent molar amount of a pharmaceutically acceptable salt thereof, (c) up to 7.5 mg/L thiamine or the equivalent molar amount of a pharmaceutically acceptable salt thereof, or (d) up to 1.0 mg/L vitamin $B_{12}$ or the equivalent molar amount of a pharmaceutically acceptable salt thereof.

In some preferred peritoneal dialysis embodiments the dialysate solution further comprises an effective amount, preferably up to 500 mg/L, of vitamin C or a pharmaceutically acceptable salt thereof.

In some preferred hemodialysis embodiments the dialysate solution further comprises an effective amount, preferably up to 1 mmol/L, of carnitine or a pharmaceutically acceptable salt thereof.

In more preferred peritoneal dialysis embodiments the dialysate solution comprises at least two nutrients or at least three nutrients selected from the group consisting of folic acid, vitamin $B_6$, thiamine, vitamin $B_{12}$, vitamin C, carnitine, and pharmaceutically acceptable salts thereof. In a most preferred embodiment the dialysate solution comprises folic acid, vitamin $B_6$, thiamine, vitamin $B_{12}$, vitamin C, and carnitine, or pharmaceutically acceptable salts thereof.

The invention also provides a dialysate solution comprising an effective amount of at least one vitamin selected from the group consisting of folic acid, vitamin $B_6$, thiamine, vitamin $B_{12}$, and pharmaceutically acceptable salts thereof. In some preferred embodiments the dialysate solution further comprises an effective amount of vitamin C or a pharmaceutically acceptable salt thereof; in some preferred embodiments the dialysate solution further comprises an effective amount of carnitine or a pharmaceutically acceptable salt thereof. The dialysate solution may be a hemodialysis solution or a peritoneal dialysis solution.

In more preferred embodiments the dialysate solution comprises at least two or at least three nutrients selected from the group consisting of folic acid, vitamin $B_6$, thiamine, vitamin $B_{12}$, vitamin C, carnitine, and pharmaceutically acceptable salts thereof. In a most preferred embodiment the dialysate solution comprises folic acid, vitamin $B_6$, thiamine, vitamin $B_{12}$, vitamin C, and carnitine, or pharmaceutically acceptable salts thereof.

The invention further provides a vitamin concentrate solution for use in a dialysate solution comprising at least one vitamin selected from the group consisting of folic acid, vitamin $B_6$, thiamine, vitamin $B_{12}$, and pharmaceutically acceptable salts thereof. In some preferred embodiments the vitamin concentrate solution further comprises vitamin C or a pharmaceutically acceptable salt thereof. In some preferred embodiments the vitamin concentrate solution further comprises carnitine or a pharmaceutically acceptable salt thereof. In a more preferred embodiment the vitamin concentrate comprises at least two or at least three nutrients selected from the group consisting of folic acid, vitamin $B_6$, thiamine, vitamin $B_{12}$, vitamin C, carnitine, and pharmaceutically acceptable salts thereof. In a most preferred embodiment the vitamin concentrate solution comprises folic acid, vitamin $B_6$, thiamine, vitamin $B_{12}$, vitamin C, and carnitine, or pharmaceutically acceptable salts thereof.

In some embodiments the invention provides a method for preventing or correcting a vitamin deficiency in a dialysis patient comprising dialysis of the patient with a dialysate solution which comprises an effective amount of at least one vitamin selected from the group consisting of folic acid, vitamin $B_6$, thiamine, vitamin $B_{12}$, and pharmaceutically acceptable salts thereof, wherein the dialysate solution further comprises at least one iron salt.

In other embodiments the invention provides a method for preventing or correcting a vitamin deficiency in a dialysis patient comprising dialysis of the patient with a dialysate solution which comprises an effective amount of at least one vitamin selected from the group consisting of folic acid, vitamin $B_6$, thiamine, vitamin $B_{12}$, and pharmaceutically acceptable salts thereof, wherein the dialysate solution further comprises at least one trace element selected from the group consisting of arsenic, rubidium, bromine, zinc, and pharmaceutically acceptable salts thereof.

The invention also constitutes the use of at least one vitamin selected from the group consisting of folic acid, vitamin $B_6$, thiamine, vitamin $B_{12}$, and pharmaceutically acceptable salts thereof for the preparation of a dialysate solution.

Other aspects and advantages of the present invention are described in the following detailed description of the preferred embodiments thereof.

DETAILED DESCRIPTION OF THE INVENTION

The present invention relates to the administration of vitamins, carnitine, and other nutrients by addition of the nutrients to a dialysate solution for use in hemodialysis or peritoneal dialysis. The methods and compositions according to the invention may be adapted for the prevention or correction of nutritional deficiencies in dialysis patients.

A. Definitions

The following definitions, of terms used throughout the specification, are intended as an aid to understanding the scope and practice of the present invention.

"Dialysis" includes both hemodialysis and peritoneal dialysis.

A "dialysate solution" is the solution used, on the opposite side of the membrane from the patient's blood, during dialysis. A "vitamin concentrate solution for use in a dialysate solution" is a composition of at least one vitamin or a pharmaceutically acceptable salt thereof, which has been formulated such that dilution of the vitamin concentrate yields either a dialysate solution containing at least a physiological amount of the vitamin or yields a dialysate concentrate containing nutrients that upon further dilution provides the desired concentration of nutrients in the final dialysate.

A "physiological amount" of a substance is the amount needed to achieve a solution concentration within the range normally found in serum. A "supraphysiologic amount" of a substance is the amount needed to achieve a solution concentration higher than the range normally found in serum.

"Nutrient" includes vitamins, minerals, carnitine, trace elements, iron salts, and other compounds which are involved in human metabolism, and includes pharmaceutically acceptable salts thereof.

"Vitamin" is a general term for a number of unrelated organic substances that are necessary for the normal metabolic functioning of the body. Vitamins may be water soluble or fat soluble, and include but are not limited to vitamin A, vitamin $B_1$ (thiamine), vitamin $B_2$ (riboflavin), vitamin $B_6$ (including pyridoxine, pyridoxal, pyridoxamine), vitamin $B_{12}$ (cyanocobalmin), vitamin C (ascorbic acid), vitamin D, vitamin E, riboflavin, biotin, vitamin K, and folic acid.

B. Advantages of the Methods and Compositions According to the Invention

The methods and compositions according to the present invention offer many advantages to the clinician and patient alike, including an improved quality of life, improved patient compliance, cost effectiveness, a method for therapeutic high dose B-vitamin therapy via the dialysate in hyperhomocysteinemia, avoidance of excessive accumulation of vitamins, and advantages in the administration of carnitine.

1. Improved quality of life: Dialysis patients are often required to take a number of medications on a regular basis. These include anti-hypertensives, phosphate binders, iron supplements, stool softeners, vitamins and blockers of acid secretion. Dialysis patients are, therefore, often required to take 15–20 pills a day. The quality of life in dialysis patients may be improved by reducing the need for oral medications by administration of vitamins by the dialysate route during dialysis.

2. Improved patient compliance: Compliance with oral medication orders is often poor in dialysis patients, because of the large number of pills the patients are required to consume and associated gastrointestinal side effects. Administration of vitamins during dialysis avoids non-compliance with oral vitamin supplements. By using vitamin fortified dialysate, development of vitamin deficiencies secondary to noncompliance with oral vitamin supplements can be avoided.

3. Cost effectiveness: Only a small fraction of oral vitamin supplements are absorbed and therefore the bioavailability is low. The bioavailability of vitamins in the dialysate is considerably higher and therefore administration of vitamins via the dialysate is cost effective. Furthermore, L-carnitine administered via the dialysate is only a fraction of the cost of intravenous administration.

4. A method for therapeutic high dose B-vitamin therapy via the dialysate in hyperhomocysteinemia: Hyperhomocysteinemia is an important risk factor for coronary and cerebrovascular disease in the general population. Homocysteine is normally catabolized by the kidney and therefore plasma levels of homocysteine are elevated in dialysis patients. Recent studies have demonstrated that administration of folic acid and vitamins B6 and B12 in high doses leads to an approximately 30% reduction in plasma homocysteine levels over a period of 1–2 months (Bostom et al. (1996), *Kidney International* 49:147–52). Administration of high doses of these vitamins via the dialysate is cost effective due to higher bioavailability, and is also convenient for the patients.

5. Avoidance of excessive accumulation of vitamins. Dialysis patients are prescribed more liberal and wholesome diets nowadays, and some recent studies in dialysis patients receiving systematic supplementation have shown excessively high vitamin levels. By maintaining a dialysate concentration that approximates the optimal serum concentration of a vitamin, the risk of excessive accumulation is minimized. This is specially important since accumulation of folic acid or ascorbic acid may be associated with serious clinical effects.

Ascorbic acid is metabolized to oxalate and vitamin C overload leads to high circulating levels of oxalate. Chronic hemodialysis patients are known to have deposits of oxalate in heart, liver, periodontium, joints, blood vessel wall, and form urinary stones. Hyperoxalemia may increase soft tissue deposition of oxalate and thereby predispose to vascular disease, particularly small vessel disease with peripheral gangrene and severe neuropathy and myopathy.

Folate, particularly in large doses may correct the megaloblastic anemia of vitamin $B_{12}$ deficiency without altering the neurologic abnormalities of subacute combined degeneration. The neurologic manifestations may even be aggravated by folate therapy. Cobalamin deficiency can thus be masked in patients who for one reason or the other are taking large doses of folate. Dialysis patients are at risk for neuropathies secondary to uremia and or diabetes and these can be difficult to distinguish from the neuropathic manifestations of cobalamin deficiency. Furthermore, dialysis patients have anemia due to renal failure per se. Therefore, a clinical diagnosis of cobalamin deficiency is particularly difficult in dialysis patients and can be made more difficult by aggressive folate administration. High concentrations of folic acid can have a convulsant effect. Furthermore there is evidence to suggest that folic acid and anticonvulsant drugs may compete for absorption across the intestinal epithelial cell and therefore therapeutic doses of folate orally may precipitate seizures in epileptics. Oral folic acid supplements of 350 μg daily reduce zinc absorption. Zinc deficiency is commonly present in dialysis patients and leads to altered taste and loss of appetite, thereby contributing to malnutrition and consequent morbidity and mortality. The need for oral folic acid supplements can be obviated if folate is administered via the dialysate. Furthermore precise control of serum folate levels is not possible with the current practice of oral folate administration , which results in high folate levels in the majority of patients. On the other hand serum folate levels can be clamped in the optimal range by addition of folic acid to the dialysate.

Pyridoxine overdose can result in ataxia and severe neuropathy and therefore should be avoided. Pyridoxine levels can be optimized by addition of pyridoxine to the dialysate.

Excessive amounts of ingested thiamine are rapidly cleared by the kidneys and there is no evidence of toxicity by oral administration in subjects with normal renal function. Effects of excessive ingestion in patients with renal failure are not known.

6. Advantages in the administration of carnitine: Currently L-carnitine is prescribed to a minority of dialysis patients who are thought to be deficient in carnitine. Carnitine deficiency is very difficult to diagnose because the symptoms and signs of carnitine deficiency such as weakness, asthenia, heart failure, etc. are nonspecific and are also common manifestations of kidney failure. Furthermore, serum levels of carnitine are a poor test of carnitine deficiency since only 5% or less of the total body carnitine is present in the serum. Muscle biopsies are diagnostic but seldom performed. Carnitine losses during dialysis and consequently deficiency of carnitine in the muscles are universally present in dialysis patients. Knowing the pitfalls of trying to diagnose and treat carnitine deficiency, it is proposed that carnitine deficiency should be prevented from developing in all dialysis patients by addition of L-carnitine to the hemodialysis and peritoneal dialysis solutions in low subtherapeutic concentrations that are equal to or below the concentration of free carnitine in normal serum.

Administration of carnitine via the dialysate appears to offer several advantages over the current methods of treatment. Oral carnitine therapy is expensive, not of proven benefit, involves taking several pills a day for patients who are already taking several different medications, and is not recommended in dialysis patients. On the other hand intravenous administration of carnitine is extremely expensive and therefore used in less than 0.1% of the dialysis patients currently. Administration of L-carnitine via the dialysate also avoids excessive accumulation of L-carnitine. Dialysis patients are prescribed more liberal and wholesome diets nowadays, thereby increasing the amount of carnitine ingested. There is an increased risk of overaccumulation of carnitine when patients with impaired kidney function are prescribed oral, parenteral, or dialysate L-carnitine, since in subjects with normal renal function 58–65% of the administered dose is excreted in the urine. This is specially important since accumulation of L-carnitine may be associated with serious clinical effects including nausea, vomiting, abdominal cramps and diarrhea. A less frequent side-effect is body odor. Mild myasthenia manifesting as muscle weakness has been described only in uremic patients receiving carnitine. These side-effects resemble the effects of underlying uremia and therefore may confuse the clinician. By maintaining a dialysate concentration that is less than or equal to the normal serum concentration of free carnitine, the risk of excessive accumulation is minimized.

C. General Principles of Dialysis and Vitamin Homeostasis

Water soluble molecules such as folic acid, pyridoxine and carnitine diffuse from patient's blood to the dialysate and vice versa, depending on the concentration gradient across the semipermeable membrane. Therefore, the net egress of molecules from the blood compartment can be prevented if the concentration of the molecule in the dialysate solution is equal to its concentration in the serum. This principle is used to maintain sodium, potassium, calcium, chloride, bicarbonate, and magnesium homeostasis in hemodialysis patients, by addition of these molecules to the dialysate compartment in different concentrations based on the patients' needs. In accordance with this principle, if the dialysate concentration of a freely diffusible vitamin or L-carnitine is equal to the normal serum concentration the direction of net transfer will be from the dialysate to the blood compartment in a patient who is deficient in this molecule and from the blood to the dialysate compartment in a patient with vitamin overload. It should be noted that the concentration of vitamin in the dialysate should be based upon the normal serum concentration of the free and not the total vitamin. This principle is useful for supplementing water soluble vitamins, carnitine and other nutrients in chronic hemodialysis or peritoneal dialysis patients, by addition of these compounds to the dialysate solutions.

D. Compositions According to the Invention

The present invention is directed to dialysate solutions comprising at least one vitamin selected from the group consisting of folic acid, vitamin $B_6$, thiamine, vitamin $B_{12}$, and pharmaceutically acceptable salts thereof. The skilled artisan can adapt the disclosed methods and compositions to the individual needs and the desired results in the patient being treated.

Different vitamin compounds and pharmaceutically acceptable salts thereof can be used in the methods and compositions according to the invention.

Sources of thiamine include thiamine disulfide, thiamine mononitrate, thiamine phosphoric acid ester chloride, thiamine phosphoric acid ester phosphate, thiamine 1,5-salt, and thiamine triphosphoric acid ester.

As a source of folic acid, folinic acid is an intermediate product in the metabolism of folic acid; the active form into which folic acid is converted in the body, ascorbic acid being a necessary cofactor in the conversion process.

Sources of vitamin $B_6$ include pyridoxine hydrochloride, pyridoxal 5-phosphate, pyridoxamine dihydrochloride, and pyridoxal.

Cobalmin is protein bound in blood, so losses of vitamin $B_{12}$ in dialysate are expected to be low in dialysis patients. However there is evidence to suggest that hemodialysis patients should be prescribed low doses of vitamin $B_{12}$. First, the postdialysis serum levels of vitamin $B_{12}$ have been found to decrease significantly during hemofiltration treatment. Second, vitamin $B_{12}$ intake has been found to be below the recommended daily allowance in maintenance hemodialysis patients. Third, several cases of vitamin $B_{12}$ deficiency have been reported in maintenance hemodialysis patients. Fourth, the losses of cobalamin with high efficiency or high flux dialysis are not known. Fifth, Long-term effects of erythropoietin treatment on cobalamin stores have not been studied. Sixth, even with normal cobalamin stores, pharmacologic doses have been shown to improve nerve conduction velocities. Last, because of its effects on folate metabolism cobalamin might be useful in lowering plasma homocysteine levels in dialysis patients. A placebo-controlled 8 week trial of 15 mg folic acid, 100 mg vitamin $B_6$, and 1 mg vitamin $B_{12}$ led to a 25–30% reduction in plasma homocysteine levels in maintenance hemodialysis patients (Bostom et al. (1996), *Kidne International* 49:147–52). The contribution of vitamin B12 to these results is not known. Cyanocobalamin is soluble in water and it is one purpose of this invention of add cyanocobalamin or its analogs to the dialysate for the purposes of prevention and treatment of vitamin $B_{12}$ deficiency.

Other nutrients that may be added to the dialysate solution in the methods and compositions according to the invention include L-carnitine or other isomers of carnitine, other vitamins, ferric pyrophosphate and other iron salts, and trace elements.

Other vitamins include vitamins A, D, E, K, riboflavin, and pantothenic acid.

Other iron salts include ferric gluconate, ferric saccharate, ferric citrate, ferric acetate, ferric chloride, ferric fluoride, ferric iodide, ferric 12-hydroxystearate, ferric stearate, ferric subsulfate, ferric glycerophosphate, ferric hydroxide, ferric nitrate, ferric orthophosphate, ferric oxalate, ferric behenate, ferric-ammonium sulfate, ferric-o-phosphate, and ferric sodium oxalate.

Patients with kidney failure may be deficient in some trace elements and overloaded with others. The brains of dialysis patients are deficient in arsenic, rubidium, and bromine. One of the most striking findings in dialysis patients is the decrease in rubidium content of most tissues. Dialysis patients also have decreased iron content in the heart and zinc content in the muscle. Trace elements may be added to the dialysate solution in the form of water soluble salts.

The vitamins and other nutrients can be added to different components of the dialysate solution in the methods and compositions according to the invention. The vitamins and other nutrients, for example, may be added to the bicarbonate concentrate, or the acid concentrate, or may be added separately in solution or powdered form. Experimental work has shown that some vitamins are freely soluble in the bicarbonate concentrate but not the acid concentrate. Other vitamins are soluble in acidic solution. Based on the specific salts of the vitamins chosen, it is possible to increase the stability of the vitamins in solution by addition of some vitamin salts that are soluble in an acidic solution to the acid concentrate and others to the bicarbonate concentrate.

When the vitamins are added to a bicarbonate concentrate, the bicarbonate concentrate advantageously has a concentration that is 27.5 fold higher than the desired concentration in the dialysate solution, because the bicarbonate concentrate is typically diluted 27.5-fold in the final dialysate solution. When it is considered desirable that the majority of patients in the dialysis unit receive nutrients via the dialysate the nutrient mix can be added to the large container of 50–200 liter capacity that is used to make or store bicarbonate concentrate. This would obviate the need for addition of the nutrients to individual bicarbonate containers, thereby increasing efficiency in the dialysis unit. If acetate dialysate is used the concentration of vitamins in the concentrate is advantageously 34 fold higher than the desired concentration in the dialysate solution.

Vitamins and other nutrients may be added to the dialysis solutions separately or mixed together. Again, separately or together, the ingredients may be added as dry powders or in a solution form. Any of these methods of formulating the ingredients are satisfactory for producing stable clear aqueous compositions by the process of this invention. The amount of the vitamin and other nutrients is limited only by their mutual compatibility in aqueous solutions.

For aqueous solutions containing a vitamin, the pH of the solution is advantageously adjusted to maximize solubility and stability of the compound. Experimental work suggests that an acidic pH about 4.2–4.6, preferably 4.4 may be optimal for vitamin compositions according to the invention. The pH adjustment can be accomplished by any pharmaceutically acceptable organic or inorganic base or acid. In a preferred embodiment citric acid is used. If the pH is lower, e.g. 3 to 4, the stability of certain B vitamins may be adversely affected. If the pH is too high, e.g. over 4.6, greater decomposition of the vitamin $B_1$ may result. When a dry powder or aqueous solution is added to the bicarbonate concentrate, the concentration of vitamins and other nutrients in the dialysate concentrate can be adjusted so that it is slightly higher than the desired concentration during dialysis in order to compensate for degradation in the alkaline environment.

E. Use of the Invention in Hemodialysis Patients

The methods and compositions according to the invention may be used for the prevention or treatment of vitamin and other nutrient deficiencies in hemodialysis patients. To prevent deficiencies, the vitamins and other nutrients may be added to the dialysate solution for every dialysis session or may be added intermittently, e.g. once a week or once a month.

Different vitamins and nutrients are bound to different extents in plasma and this binding must be taken into consideration when practicing the invention.

Table 1 summarizes several principles for the basis of the invention, including suggested concentrations of compounds (vitamins and other nutrients) in the dialysate solution for the prevention and treatment of deficiencies.

Tables 2 and 3 show suggested concentrations of vitamins and carnitine in hemodialysate solutions for the prevention (Table 2) and treatment (Table 3) of deficiencies.

The values suggested in Tables 1–3 are suggested values only, and the skilled artisan will routinely tailor these concentrations to meet individual patient needs and to improve the efficiency of the dialysis unit.

TABLE 1

Principles For the Basis of the Invention

| | Concentration Of Compound In The Dialysate Solution For The Purpose Of | |
|---|---|---|
| Characteristic of the plasma protein binding | Prevention of deficiency by addition to dialysate with every dialysis | Treatment of deficiency or prevention of deficiency by adding intermittently (once a week-month) |
| No significant protein binding | equal to normal plasma level | up to 10–50 fold higher than the normal plasma level |
| Significant binding present and free level in the plasma is known | equal to normal plasma level of the free compound | up to 10–50 fold higher than the normal plasma level of the free compound |
| Significant binding present but the fraction bound and therefore the free level in the plasma is not known[1] | equal to [total normal plasma level] + $(V_P/V_D)_2$ | up to 10–50 fold higher than [total normal plasma level] + $(V_P/V_D)_2$ |

[1]The effects of uremia on plasma protein binding of vitamins are not known. Therefore in dialysis patients the extent of protein binding is not known for vitamins that are normally protein bound.
[2]For vitamins that bind to plasma proteins the concentration of vitamins achieved in plasma ($V_P$) should exceed the vitamin concentration in the dialysate ($V_D$) after sufficient dialysis.

TABLE 2

Hemodialysis Solutions[1] for the Prevention of Vitamin and Carnitine Deficiencies in Hemodialysis Patients

| | Fraction of the plasma content that is protein bound (%)[2] | Normal plasma concentration | Preferred concentration in the dialysate during every dialysis session for the prevention of deficiencies[3] |
|---|---|---|---|
| Folic acid | 1. low affinity binding to albumin 2. high affinity binding to glycoproteins (<5%) | 5–15 μg/L | <15 μg/L |
| Ascorbic acid (vit C) | not bound | 4–15 mg/L | <15 mg/L |
| Pyridoxal 5'-phosphate (vit $B_6$) | albumin | 3–10 μg/L | <10 μg/L |
| Thiamine | albumin | Whole blood: 20–37 μg/L Plasma[4]: 4–20 μg/L | <20 μg/L |
| Vitamin $B_{12}$ | Protein bound | Serum: 0.2–0.6 μg/L | <0.6 μg/L |
| Free L-carnitine | not bound | 20–50 μmol/L | <50 μmol/L |

[1]The concentration of the nutrients in the concentrate is proportionately higher so that upon dilution the final concentration in the dialysate solution is appropriate. For the Fresenius system, for example, the concentration of compound in bicarbonate concentrate is 27.5 times the desired concentration in the dialysate and if acetate dialysate is used the concentration of vitamins in the concentrate should be 34 fold higher than the desired concentration in the dialysate.
[2]The binding of compounds to plasma proteins may be altered in uremia. The uremic toxins may displace some compounds from their binding sites on plasma proteins (e.g. dilantin). Effects of uremia on the plasma protein binding of the above vitamins have not been examined.
[3]The highest concentration of the compound in the dialysate for prevention of deficiency has been chosen as upper limit of normal serum level. However there may be chemical degradation of the vitamins in the dialysis concentrate if the solution is not used immediately after the addition of the vitamins due to light sensitivity or chemical interaction between the different compounds. The concentrations of the vitamins in the concentrate may therefore be increased to compensate for this potential loss of vitamins.
[4]A fraction of the whole blood thiamine is found in the plasma. Most of the thiamine in plasma may be bound to albumin (in subjects with normal kidney function).

TABLE 3

Hemodialysis Solutions[1] for the Treatment of Vitamin and Carnitine Deficiencies in Hemodialysis Patients

| | Plasma concentrations reported in hemodialysis patients receiving supplementation in high doses | Preferred concentration in the dialysate for the treatment of deficiencies[2] |
|---|---|---|
| Folic acid | 927 ± 575 μg/L with 15 mg folic acid daily for 8 weeks[3] | 15 μg/L–1500 μg/L |
| Ascorbic acid (vitamin C) | 28 ± 2 mg/L (mean ± SE), Range: 15–37 mg/L, with 500 mg ascorbic acid/day for 2 weeks[4] | up to 40 mg/L |
| Pyridoxine or Pyridoxal 5'-Phosphate (vit $B_6$) | 45 ± 36 μg/L with 100 mg $B_6$/day for 8 weeks[3] | up to 100 μg/L |

TABLE 3-continued

Hemodialysis Solutions[1] for the Treatment of Vitamin and Carnitine Deficiencies in Hemodialysis Patients

| | Plasma concentrations reported in hemodialysis patients receiving supplementation in high doses | Preferred concentration in the dialysate for the treatment of deficiencies[2] |
|---|---|---|
| Thiamine | Whole blood thiamine 50 ± 12 µg/L with 600–900 mg thiamine per week[5] | up to 75 µg/L |
| Vitamin $B_{12}$ | 1.3 ± 0.4 µg/L[3] | up to 60 µg/L |
| L-carnitine | Free carnitine 250 ± 11 µmol/L (mean ± SE) on 20 mg/Kg of L-carnitine intravenously three times a week following hemodialysis for 6 months[6] | 50–300 µmol/L |

[1]Unless reported otherwise all values are predialysis values expressed as mean ± SD
[2]It may be more convenient and feasible to add a large amount of the compound during a single dialysis session (e.g. once a week) rather than during every dialysis. Therefore, these higher concentrations may also be needed for prevention when used intermittently in addition to being needed for treatment of deficiencies.
[3]Bostom et al. (1996), Kidney International 49:147–52.
[4]A Ponka, B Kuhlback (1983), Acta Medica Scandinavica 213:305–7
[5]E Descombes, AB Hanck, G Fellay (1993), Kidney International 43:1319–28.
[6]TA Golper et al. (1990), Kidney International 38:904–11.

F. Use of the Invention in Peritoneal Dialysis Patients

Peritoneal dialysis patients commonly use 3–10 exchanges per day depending on the type of peritoneal dialysis treatment. Addition of vitamins and other nutrients to every bag of peritoneal dialysis solution by the patient may increase the risk of contamination, thereby introducing infection leading to peritonitis. To avoid this complication drugs such as antibiotics are often administered to the patient in large supraphysiologic amounts added to the bag that dwells overnight, instead of small amounts added to every exchange. Therefore, vitamins, carnitine, and other nutrients are advantageously added in high concentrations to sporadic bags either to prevent deficiency from intradialytic loss of vitamins or to correct such a deficiency state.

EXAMPLES

The following examples illustrate the invention. These examples are illustrative only, and do not limit the scope of the invention.

Example 1

Preparation and Use of Vitamin Concentrate Solutions

A. Preparation of a Vitamin Concentrate Solution

A vitamin concentrate solution was prepared according to the formulation shown on Table 4.

TABLE 4

| Ingredient | Amount per 250 ml |
|---|---|
| Thiamine HCl | 65.06 mg |
| Folic acid | 26.024 mg |
| Ascorbic acid | 26.024 g |
| Pyridoxine HCl | 26;024 mg |

B. Preparation of a Vitamin Concentrate Solution with Iron

A vitamin concentrate solution with iron was prepared according to the formulation shown on Table 5.

TABLE 5

| Ingredient | Amount per 250 ml |
|---|---|
| Ferric pyrophosphate | 2.750 mg |
| Thiamine HCl | 65.06 mg |
| Folic acid | 26.024 mg |
| Ascorbic acid | 26.024 g |
| Pyridoxine HCl | 26.024 mg |

C. Preparation of a Vitamin Concentrate Solution with Carnitine

L-carnitine (2.6 mmoles) is added to solutions in example 1 or 2 either as a dry powder or as a solution.

D. Use of a Vitamin Concentrate Solutions to Prepare a Dialysate Solution

A vitamin concentrate solution according to Example 1A, 1B, or 1C is adjusted to pH 4.4 using citric acid. The 250 ml vitamin concentrate solution is added to 25 gallons (i.e., 10 ml is added per gallon) of bicarbonate concentrate for hemodialysis to make a vitamin plus bicarbonate concentrate. One part of the vitamin plus bicarbonate concentrate is diluted with 27.5 parts of acid concentrate and water (1:32.77) to prepare the dialysate solution.

Example 2

Dialysis of Uremic Plasma

To determine the concentration of a vitamin or other nutrient in the dialysate that is needed to maintain the serum level in the normal range, it is important to know the plasma concentration of the freely filterable vitamin. However, uremic toxins may alter the binding of vitamins to plasma proteins. In uremic subjects, the proportion of the total plasma vitamin that is free is not known. In the following experiment uremic plasma was dialyzed against dialysate solutions containing different concentrations of vitamins, and the total plasma levels of vitamins after dialysis was measured.

Plasma obtained from a uremic subject undergoing plasmapheresis was pooled and samples were taken for estimation of baseline vitamin levels. The total volume of 2.7 liters was divided into three equal aliquots of 900 ml each. Hemodialysis was performed on each aliquot of plasma using a F-60 polysulfone dialyzer (Fresenius Inc., USA). The plasma flow rate was 350 ml/min and the dialysate flow rate was 500 ml/min.

In the first experiment, vitamins were not added to the dialysate. In the second experiment, vitamins were added to the dialysate at a concentration that was close to the upper limit of normal, to simulate the maintenance of physiologic levels. In the third experiment, vitamins were added to the dialysate at a concentration that was 10 times that in the second experiment, with the aim of achieving supratherapeutic levels. The results of the three experiments are summarized in Table 6.

TABLE 6

In Vitro Hemodialysis of Uremic Plasma Using Dialysate Solutions With and Without the Addition of Vitamins

| Concentration of vitamin in the dialysate | Plasma concentration of the vitamin after dialysis for | | | Ratio of Plasma to dialysate at the end of dialysis ($V_P/V_D$) |
|---|---|---|---|---|
| | 0 min (Baseline) | 45 min | 90 min | |
| Folic Acid | | | | |
| 0 µg/L | 5.8 µg/L | 1.7 µg/L | 3.3 µg/L | not applicable |
| 15 µg/L | 5.8 µg/L | 32.2 µg/L | 39.8 µg/L | 2.6 |
| 150 µg/L | 5.8 µg/L | 256.5 µg/L | 272.2 µg/L | 1.8 |
| Thiamine ($B_1$) | | | | |
| 0 µg/L | 17 µg/L | not done | 3.6 µg/L | not applicable |
| 60 µg/L | 17 µg/L | not done | 72 µg/L | 1.2 |
| 600 µg/L | 17 µg/L | not done | >100 µg/L | not estimated |

The plasma pyridoxal 5-phosphate (PLP) concentration decreased from 5.2 µg/L to 3.1–3.7 µg/L after 90 minutes of dialysis. Addition of pyridoxine hydrochloride to the dialysate did not result in an increase in PLP concentration since the assay used is specific for esters such as PLP and does not measure pyridoxine.

It is expected that following termination of dialysis with vitamin containing dialysate there will be tissue uptake and metabolism of the vitamins, thereby leading to a progressive fall in the plasma vitamin concentration that may continue to occur till the time of the next dialysis session. Therefore, it would be desirable to attain a total plasma vitamin concentration that is close to the upper limit of normal towards the end of a hemodialysis session. For the vitamins that are bound partly to plasma proteins, the total plasma level of vitamins achieved is higher than the level of the vitamins in the dialysate (see table 1). However the efficiency of diffusive transport across the dialyzer membrane is determined partly readily compared to larger compounds. Therefore dialysate vitamin concentration needs by the molecular weight of the compound. Smaller compounds cross more to be determined separately for every vitamin. The required dialysate vitamin concentration may be derived by dividing the desired plasma concentration by the plasma to dialysate vitamin gradient ($V_P/V_D$).

Example 3

Vitamin and Carnitine Delivery Via Dialysate in a Maintenance Hemodialysis Patient with End-Stage Kidney Failure The following example illustrates how the methods and compositions according to the invention are used in a maintenance hemodialysis patient, and is applicable to every maintenance hemodialysis patient.

A powdered mixture of vitamins and L-carnitine is available in the hemodialysis unit in an amber vial containing 1.03 milligrams folic acid, 1.3 grams ascorbic acid, 0.7 milligrams pyridoxine hydrochloride, 2 milligrams thiamine, 70 micrograms cobalamin, and 660 milligrams L-carnitine. Just prior to starting dialysis the dialysis technician empties two of these vials into a plastic container with 10 liters of a concentrated solution of sodium bicarbonate (bicarbonate concentrate). The technician rocks the container back and forth 5 times. The powder readily goes into solution and the solution turns a light orange color due to the color of folic acid. The technician starts the hemodialysis machine (Fresenius Inc., USA). The automated proportioning system in the machine mixes 1.23 parts of the bicarbonate concentrate with 1 part of a concentrated acidic solution (containing NaCl, KCl, CaCl2, Na-acetate, and glucose) and 32.77 parts of pure water, thereby generating the final dialysate solution. The final dialysate solution contains 7.5 µg folic acid, 10 mg ascorbic acid, 5 µg pyridoxine, 15 µg thiamine, and 4.8 mg L-carnitine per liter of solution.

The patient has end-stage kidney failure and is on maintenance hemodialysis. His blood is circulated at a rate of 450 ml/min through a F-80 polysulphone dialyzer (Fresenius Inc., USA) and dialyzed against the vitamin and L-carnitine containing dialysate flowing into the dialyzer at a rate of 800 ml/min. The patient is dialyzed for 4 hours three times a week using the same procedure for generating vitamin and L-carnitine fortified dialysate. The patient therefore does not require oral vitamin supplements which are stopped. The patient had been poorly compliant with his medications, and consequently regular dialysate vitamin supplementation leads to an improvement in his general condition. With time there is also an improvement in cardiac function, hyperhomocysteinemia and neuropathy, and a decrease in the erythropoietin requirement.

When it is considered desirable that the majority of patients in the dialysis unit receive vitamins and other nutrients via the dialysate, the vitamin and nutrient mix can be added to a large container (e.g., 50–200 liter capacity) that is used to make or store bicarbonate concentrate. This obviates the need for addition of vitamins and nutrients to individual bicarbonate containers, thereby increasing efficiency in the dialysis unit.

Example 4

Modification of the Nutrient Mix to Meet the Special Requirements of an Individual Patient The following example illustrates how the methods and compositions according to the invention are modified for an individual patient.

A hemodialysis patient with diabetes, hypertension, and coronary artery disease develops transient ischemic attacks. His cholesterol is found to be normal but the plasma homocysteine is twice the upper limit of normal. The hyperhomocysteinemia is present despite regular administration of standard doses of folic acid and pyridoxine orally. The patient is prescribed supraphysiologic doses of oral folic acid (15 mg/day), vitamins $B_6$ (100 mg/day), and $B_{12}$ (1 mg/day). The patient, however, is non-compliant with this regimen due to associated gastrointestinal side-effects and the increased number of pills that he is required to take. The patient is therefore prescribed high doses of folic acid, $B_{12}$ and $B_6$ via the dialysate (See Table 3), leading to normalization of homocysteine levels over a period of 3 months.

Example 5

Vitamin and Carnitine Supplementation Via Peritoneal Dialysis Solution

A diabetic patient receiving peritoneal dialysis has coronary artery disease, hyperhomocysteinemia, progressive peripheral sensorimotor neuropathy, diabetic gastroparesis and malnutrition. The patient does not tolerate oral medications due to gastroparesis and vomiting. The patient comes to the dialysis clinic every 3 weeks for a follow up. Upon his clinic visit the dialysis nurse adds a concentrated sterile solution of vitamins and L-carnitine containing 10 mg folic acid, 1 mg vitamin $B_{12}$, 500 mg vitamin C, 5 mg thiamine, 10 mg pyridoxine, and 600 µmol of L-carnitine to a 2 liter (2 L) bag of peritoneal dialysis solution. This bag is infused into the patients peritoneal cavity and patient is instructed to drain it out after 6 hours. The procedure is repeated every 3 weeks during his regular clinic visit. The patient is able to discontinue his oral vitamin supplements and with time there is improvement in his general condition, appetite, nutritional status and a decline in the plasma homocysteine levels.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

I claim:

1. A method for preventing or correcting a vitamin deficiency in a dialysis patient comprising dialysis of the patient with a dialysate solution which comprises an effective amount of at least one vitamin selected from the group consisting of folic acid, vitamin $B_6$, thiamine, vitamin $B_{12}$, and pharmaceutically acceptable salts thereof, wherein the at least one vitamin is present in the dialysate solution in an amount less than a physiological amount or in a supraphysiologic amount.

2. The method of claim 1 wherein the dialysis is hemodialysis.

3. The method of claim 2 wherein the dialysate solution comprises up to 1500 µg/L folic acid or the equivalent molar amount of a pharmaceutically acceptable salt thereof.

4. The method of claim 3 wherein the dialysate solution comprises up to 15 µg/L folic acid or the equivalent molar amount of a pharmaceutically acceptable salt thereof.

5. The method of claim 2 wherein the dialysate solution comprises up to 100 µg/L vitamin $B_6$ or the equivalent molar amount of a pharmaceutically acceptable salt thereof.

6. The method of claim 5 wherein the dialysate solution comprises up to 10 µg/L vitamin $B_6$ or the equivalent molar amount of a pharmaceutically acceptable salt thereof.

7. The method of claim 2 wherein the dialysate solution comprises up to 75 µg/L thiamine or the equivalent molar amount of a pharmaceutically acceptable salt thereof.

8. The method of claim 7 wherein the dialysate solution comprises up to 20 µg/L thiamine or the equivalent molar amount of a pharmaceutically acceptable salt thereof.

9. The method of claim 2 wherein the dialysate solution comprises up to 60 µg/L vitamin $B_{12}$ or the equivalent molar amount of a pharmaceutically acceptable salt thereof.

10. The method of claim 9 wherein the dialysate solution comprises up to 0.6 µg/L vitamin $B_{12}$ or the equivalent molar amount of a pharmaceutically acceptable salt thereof.

11. The method of claim 1 wherein the vitamin deficiency is prevented by adding less than a physiological amount of the at least one vitamin to the dialysate solution.

12. The method of claim 1 wherein the vitamin deficiency is prevented or corrected by adding a supraphysiologic amount of the at least one vitamin to the dialysate solution.

13. The method of claim 1 wherein the dialysate solution further comprises an effective amount of vitamin C or a pharmaceutically acceptable salt thereof.

14. The method of claim 13 wherein the dialysate solution comprises up to 40 mg/L vitamin C or the equivalent molar amount of a pharmaceutically acceptable salt thereof.

15. The method of claim 14 wherein the dialysate solution comprises up to 15 mg/L vitamin C or the equivalent molar amount of a pharmaceutically acceptable salt thereof.

16. The method of claim 1 wherein the dialysate solution further comprises an effective amount of carnitine or a pharmaceutically acceptable salt thereof.

17. The method of claim 16 wherein the dialysate solution comprises up to 300 µmol/L carnitine or the equivalent molar amount of a pharmaceutically acceptable salt thereof.

18. The method of claim 17 wherein the dialysate solution comprises up to 50 µmol/L carnitine or the equivalent molar amount of a pharmaceutically acceptable salt thereof.

19. The method of claim 1 wherein the dialysate solution comprises at least two nutrients selected from the group consisting of folic acid, vitamin $B_6$, thiamine, vitamin $B_{12}$, vitamin C, carnitine, and pharmaceutically acceptable salts thereof.

20. The method of claim 19 wherein the dialysate solution comprises at least three nutrients selected from the group consisting of folic acid, vitamin $B_6$, thiamine, vitamin $B_{12}$, vitamin C, carnitine, and pharmaceutically acceptable salts thereof.

21. The method of claim 20 wherein the dialysate solution comprises folic acid, vitamin $B_6$, thiamine, vitamin $B_{12}$, vitamin C, and carnitine, or pharmaceutically acceptable salts thereof.

22. The method of claim 1 wherein the dialysis is peritoneal dialysis.

23. The method of claim 22 wherein the vitamin deficiency is prevented by adding at least a physiological amount of the vitamin to the dialysate solution.

24. The method of claim 22 wherein the vitamin deficiency is corrected by adding a supraphysiologic amount of the vitamin to the dialysate solution.

25. The method of claim 22 wherein the dialysate solution comprises up to 15 mg/L folic acid or the equivalent molar amount of a pharmaceutically acceptable salt thereof.

26. The method of claim 22 wherein the dialysate solution comprises up to 10 mg/L vitamin $B_6$ or the equivalent molar amount of a pharmaceutically acceptable salt thereof.

27. The method of claim 22 wherein the dialysate solution comprises up to 7.5 mg/L thiamine or the equivalent molar amount of a pharmaceutically acceptable salt thereof.

28. The method of claim 22 wherein the dialysate solution comprises up to 1.0 mg/L vitamin $B_{12}$ or the equivalent molar amount of a pharmaceutically acceptable salt thereof.

29. The method of claim 22 wherein the dialysate solution further comprises an effective amount of vitamin C or a pharmaceutically acceptable salt thereof.

30. The method of claim 29 wherein the dialysate solution comprises up to 500 mg/L vitamin C or the equivalent molar amount of a pharmaceutically acceptable salt thereof.

31. The method of claim 22 wherein the dialysate solution further comprises an effective amount of carnitine or a pharmaceutically acceptable salt thereof.

32. The method of claim 31 wherein the dialysate solution comprises up to 1 mmol/L carnitine or the equivalent molar amount of a pharmaceutically acceptable salt thereof.

33. The method of claim 22 wherein the dialysate solution comprises at least two nutrients selected from the group consisting of folic acid, vitamin $B_6$, thiamine, vitamin $B_{12}$, vitamin C, carnitine, and pharmaceutically acceptable salts thereof.

34. The method of claim 33 wherein the dialysate solution comprises at least three nutrients selected from the group consisting of folic acid, vitamin $B_6$, thiamine, vitamin $B_{12}$, vitamin C, carnitine, and pharmaceutically acceptable salts thereof.

35. The method of claim 34 wherein the dialysate solution comprises folic acid, vitamin $B_6$, thiamine, vitamin $B_{12}$, vitamin C, and carnitine, or pharmaceutically acceptable salts thereof.

36. The method of claim 1 wherein the dialysate solution further comprises at least one iron salt.

37. The method of claim 36 wherein the iron salt is ferric pyrophosphate.

38. The method of claim 1 wherein the dialysate solution further comprises at least one trace element selected from the group consisting of arsenic, rubidium, bromine, zinc, and pharmaceutically acceptable salts thereof.

39. The method of claim 1 wherein the amount less than the physiological amount is equal to the total normal plasma level concentration of the at least one vitamin÷$(V_p/V_D)^2$.

40. The method of claim 1 wherein the supraphysiologic amount is up to 10–50 fold higher than the total normal plasma level concentration of the at least one vitamin÷$(V_p/V_D)^2$.

* * * * *

(12) EX PARTE REEXAMINATION CERTIFICATE (7978th)
United States Patent
Gupta

(10) Number: US 6,537,976 C1
(45) Certificate Issued: Jan. 11, 2011

(54) DIALYSIS SOLUTIONS CONTAINING WATER SOLUBLE VITAMINS AND NUTRIENTS

(75) Inventor: Ajay Gupta, Farmington Hills, MI (US)

(73) Assignee: Charak LLC, Cerritos, CA (US)

Reexamination Request:
No. 90/009,162, May 30, 2008

Reexamination Certificate for:
Patent No.: 6,537,976
Issued: Mar. 25, 2003
Appl. No.: 09/367,629
Filed: Oct. 18, 1999

(22) PCT Filed: Aug. 6, 1998

(86) PCT No.: PCT/US98/16383
§ 371 (c)(1),
(2), (4) Date: Oct. 18, 1999

(87) PCT Pub. No.: WO99/07419
PCT Pub. Date: Feb. 18, 1999

Related U.S. Application Data

(60) Provisional application No. 60/055,015, filed on Aug. 7, 1997.

(51) Int. Cl.
*A61K 45/06* (2006.01)
*A61K 31/70* (2006.01)
*A61K 45/00* (2006.01)
*A61M 1/16* (2006.01)

(52) U.S. Cl. ............................................ 514/52; 604/29
(58) Field of Classification Search .................. None
See application file for complete search history.

(56) References Cited

U.S. PATENT DOCUMENTS

| 4,237,167 A | | 12/1980 | Cavazza | |
|---|---|---|---|---|
| 4,308,255 A | * | 12/1981 | Raj et al. | ............... 424/677 |
| 4,756,838 A | * | 7/1988 | Veltman | ............... 424/490 |

FOREIGN PATENT DOCUMENTS

| AU | 615553 | 1/1990 |
|---|---|---|
| EP | 0347714 | 12/1989 |
| WO | 93/24108 | 12/1993 |

OTHER PUBLICATIONS

"Ascorbic Acid Depletion During Hemodialysis" by Sullivan, J.F. et al., JAMA, vol. 220, No. 13, pp. 1697–1699 (Jun. 1972).

"L–carnitine addition to dialysis fluid. A therapeutic alternative for hemodialysis patients" by Vacha, G.M. et al., Nephron, vol. 51, No. 2, pp. 237–242 (1989).

* cited by examiner

*Primary Examiner*—Evelyn Huang

(57) ABSTRACT

The invention relates to methods and compositions for the prevention and treatment of vitamin and other nutrient deficiencies in hemodialysis and peritoneal dialysis patients. Patients are dialyzed with a dialysate solution comprising at least one vitamin.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-40 are cancelled.

* * * * *